(12) United States Patent
Layman et al.

(10) Patent No.: US 8,795,254 B2
(45) Date of Patent: Aug. 5, 2014

(54) MEDICAL DEVICES WITH A SLOTTED TUBULAR MEMBER HAVING IMPROVED STRESS DISTRIBUTION

(75) Inventors: Ted Layman, Park City, UT (US); Clay W. Northrop, Salt Lake City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 667 days.

(21) Appl. No.: 12/635,577

(22) Filed: Dec. 10, 2009

(65) Prior Publication Data

US 2010/0145308 A1 Jun. 10, 2010

Related U.S. Application Data

(60) Provisional application No. 61/121,510, filed on Dec. 10, 2008.

(51) Int. Cl.
*A61M 25/00* (2006.01)
*A61B 5/00* (2006.01)

(52) U.S. Cl.
USPC ............................ 604/524; 600/585; 604/523

(58) Field of Classification Search
USPC .......................................... 600/585; 604/523
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |

(Continued)

FOREIGN PATENT DOCUMENTS

| | | |
|---|---|---|
| EP | 0 215 173 | 3/1987 |
| EP | 0 377 453 | 7/1990 |

(Continued)

OTHER PUBLICATIONS

H.A. Rothbart, "Helical Compression Springs", Mechanical Design and Systems Handbook, 1964, p. 33-13 (one sheet).

*Primary Examiner* — Max Hindenburg
*Assistant Examiner* — Adam Eiseman
(74) *Attorney, Agent, or Firm* — Seager, Tufte & Wickhem, LLC

(57) ABSTRACT

Medical devices and methods for making and using the same. A medical device may include an elongate tubular member. The tubular member may include a first circumferential tube segment, a second circumferential tube segment disposed next to the first circumferential tube segment, and a third circumferential tube segment disposed next to the second circumferential tube segment. The first tube segment and the second tube segment may be separated by a first set of slots formed in the tubular member. The second tube segment and the third tube segment may be separated by a second set of slots formed in the tubular member. The second tube segment may be connected to the first tube segment with a proximally-extending beam formed in the tubular member. The second tube segment may also be connected to the third tube segment with a distally-extending beam formed in the tubular member. A ring may be defined in the second tube segment between the proximally-extending beam and the distally-extending beam. The ring may have a first portion with a first width and a second portion with a second width different from the first width.

20 Claims, 9 Drawing Sheets

(56) References Cited

U.S. PATENT DOCUMENTS

| | | |
|---|---|---|
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,973,321 A | 11/1990 | Michelson |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,228,453 A | 7/1993 | Sepetka |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,049 A | 11/1994 | Raman et al. |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,409,015 A | 4/1995 | Palermo |
| 5,411,476 A | 5/1995 | Abrams |
| 5,425,723 A | 6/1995 | Wang |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A * | 4/1996 | Goode et al. .................. 606/108 |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |

(56) References Cited

U.S. PATENT DOCUMENTS

| | | |
|---|---|---|
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,605,543 A | 2/1997 | Swanson |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,902,499 A | 5/1999 | Richerzhagen |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,955,640 A | 9/1999 | Paludetto et al. |
| 5,971,975 A | 10/1999 | Mills et al. |
| 5,980,471 A | 11/1999 | Jafari |
| 5,997,487 A | 12/1999 | Kolehmainen et al. |
| 6,001,068 A | 12/1999 | Uchino et al. |
| 6,004,279 A | 12/1999 | Crowley et al. |
| 6,007,478 A | 12/1999 | Siess et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,071,305 A | 6/2000 | Brown et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| RE37,148 E | 4/2001 | Shank |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,383,146 B1 | 5/2002 | Klint |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B1 | 4/2003 | Smits |
| 6,579,246 B2 * | 6/2003 | Jacobsen et al. ............... 600/585 |
| 6,602,207 B1 | 8/2003 | Mann et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,673,025 B1 | 1/2004 | Richardson et al. |
| 6,682,493 B2 | 1/2004 | Mirigian |
| 6,689,120 B1 | 2/2004 | Gerdts |

(56) References Cited

U.S. PATENT DOCUMENTS

| | | |
|---|---|---|
| 6,702,762 B2 | 3/2004 | Jafari et al. |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,071,197 B2 | 7/2006 | Leonardi et al. |
| 7,074,197 B2 | 7/2006 | Reynolds et al. |
| 7,153,277 B2 | 12/2006 | Skujins et al. |
| 7,169,118 B2 | 1/2007 | Reynolds et al. |
| 7,182,735 B2 | 2/2007 | Shireman et al. |
| 7,618,379 B2 | 11/2009 | Reynolds et al. |
| 7,914,466 B2 * | 3/2011 | Davis et al. ............... 600/585 |
| 8,246,574 B2 * | 8/2012 | Jacobs et al. ............ 604/95.01 |
| 2002/0019599 A1 | 2/2002 | Rooney et al. |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |
| 2003/0216668 A1 | 11/2003 | Howland et al. |
| 2004/0116831 A1 | 6/2004 | Vrba |
| 2004/0142643 A1 | 7/2004 | Miller et al. |
| 2004/0167437 A1 * | 8/2004 | Sharrow et al. ............... 600/585 |
| 2004/0167441 A1 | 8/2004 | Reynolds et al. |
| 2004/0181174 A2 | 9/2004 | Davis et al. |
| 2004/0181176 A1 | 9/2004 | Jafari et al. |
| 2005/0115624 A1 | 6/2005 | Walak |
| 2006/0121218 A1 | 6/2006 | Obara et al. |
| 2006/0189896 A1 | 8/2006 | Davis et al. |
| 2006/0264904 A1 | 11/2006 | Kerby et al. |
| 2007/0100285 A1 | 5/2007 | Griffin et al. |
| 2007/0100374 A1 | 5/2007 | Vrba |
| 2007/0100424 A1 | 5/2007 | Chew et al. |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0064989 A1 | 3/2008 | Chen et al. |
| 2008/0077119 A1 | 3/2008 | Snyder et al. |
| 2009/0043283 A1 | 2/2009 | Turnland et al. |

FOREIGN PATENT DOCUMENTS

| | | |
|---|---|---|
| EP | 0 778 039 | 6/1997 |
| EP | 0 937 481 | 8/1999 |
| EP | 0 790 066 | 4/2000 |
| EP | 0 608 853 | 4/2003 |
| GB | 2257269 | 1/1993 |
| JP | 58-8522 | 1/1983 |
| JP | 62-299277 | 12/1987 |
| JP | 1-135363 | 5/1989 |
| JP | 1-158936 | 6/1989 |
| JP | 2-107268 | 4/1990 |
| JP | 03-122850 | 12/1991 |
| JP | 4-061840 | 2/1992 |
| JP | 5-506806 | 10/1993 |
| JP | 5-309519 | 11/1993 |
| JP | 6-31749 | 4/1994 |
| JP | 6-63224 | 9/1994 |
| JP | 6-312313 | 11/1994 |
| JP | 7-124164 | 5/1995 |
| JP | 7-124263 | 5/1995 |
| JP | 7-136280 | 5/1995 |
| JP | 7148264 | 6/1995 |
| JP | 7037199 | 7/1995 |
| JP | 7185009 | 7/1995 |
| JP | 7275366 | 10/1995 |
| JP | 751067 | 11/1995 |
| JP | 8509141 | 10/1996 |
| JP | 8-317988 | 12/1996 |
| JP | 9000164 | 4/1997 |
| JP | 9-276413 | 10/1997 |
| JP | 10-118193 | 5/1998 |
| JP | 2000-197704 A | 7/2000 |
| WO | WO 90/02520 | 3/1990 |
| WO | WO 95/32834 | 12/1995 |
| WO | WO 96/38193 | 12/1996 |
| WO | WO 97/44086 | 11/1997 |
| WO | WO 99/11313 | 3/1999 |
| WO | WO 02/13682 | 2/2002 |
| WO | WO 2004/047899 | 6/2004 |

* cited by examiner

MEDICAL DEVICES WITH A SLOTTED TUBULAR MEMBER HAVING IMPROVED STRESS DISTRIBUTION

CROSS-REFERENCE TO RELATED APPLICATIONS

This application claims the benefit of U.S. Provisional Application No. 61/121,510, filed Dec. 10, 2008, the entire disclosure of which is incorporated herein by reference.

FIELD OF THE INVENTION

The present invention pertains to medical devices, and methods for manufacturing medical devices. More particularly, the present invention pertains to elongated intracorporeal medical devices including a slotted tubular member and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices and tubular members for use in medical devices. An example medical device may include an elongate tubular member. The tubular member may include a first circumferential tube segment, a second circumferential tube segment disposed next to the first circumferential tube segment, and a third circumferential tube segment disposed next to the second circumferential tube segment. The first tube segment and the second tube segment may be separated by a first set of slots formed in the tubular member. The second tube segment and the third tube segment may be separated by a second set of slots formed in the tubular member. The second tube segment may be connected to the first tube segment with a proximally-extending beam formed in the tubular member. The second tube segment may also be connected to the third tube segment with a distally-extending beam formed in the tubular member. A ring may be defined in the second tube segment between the proximally-extending beam and the distally-extending beam. The ring may have a first portion with a first width and a second portion with a second width different from the first width.

Another example medical device may include an elongate tubular member. The tubular member may include a plurality of circumferential tube segments that are each defined between two longitudinally-adjacent sets of slots formed in the tubular member. Longitudinally-adjacent tube segments may be connected together by flanking sets of beams that are disposed on opposite sides of each tube segment. Each tube segment may include one or more rings that are defined between a pair of beams on opposing sides of the tube segment. At least one of the one or more rings may have a varying width.

An example slotted tubular member for use in a medical device may include a first circumferential tube segment, a second circumferential tube segment disposed next to the first circumferential tube segment, and a third circumferential tube segment disposed next to the second circumferential tube segment. A proximally-extending beam may be formed in the tubular member and may extend between the first tube segment and the second tube segment. A distally-extending beam may be formed in the tubular member and may extend between the second tube segment and the third tube segment. A ring may be defined in the second tube segment between the proximally-extending beam and the distally-extending beam. The ring may have a varying width.

An example method for manufacturing a medical device may include providing an elongate tubular member and forming a plurality of slots in the tubular member. The tubular member may include a first circumferential tube segment, a second circumferential tube segment disposed next to the first circumferential tube segment, and a third circumferential tube segment disposed next to the second circumferential tube segment. The first tube segment and the second tube segment may be separated by a first set of slots formed in the tubular member. The second tube segment and the third tube segment may be separated by a second set of slots formed in the tubular member. The second tube segment may be connected to the first tube segment with a proximally-extending beam formed in the tubular member. The second tube segment may also be connected to the third tube segment with a distally-extending beam formed in the tubular member. A ring may be defined in the second tube segment between the proximally-extending beam and the distally-extending beam. The ring may have a first portion with a first width and a second portion with a second width different from the first width.

Another example medical device may include a slotted tubular member including a plurality of tube segments interconnected by beams disposed on opposite sides of the tube segments. A ring may be defined in the tubular member between the beams disposed on opposite sides of one of tube segments. The ring may have a varying width.

Another example medical device may include a slotted tubular member including a plurality of tube segments interconnected by beams disposed on opposite sides of the tube segments. A ring may be defined in the tubular member between the beams disposed on opposite sides of one of tube segments. The ring may be configured to distribute stress in a substantially uniform manner throughout the tubular member.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
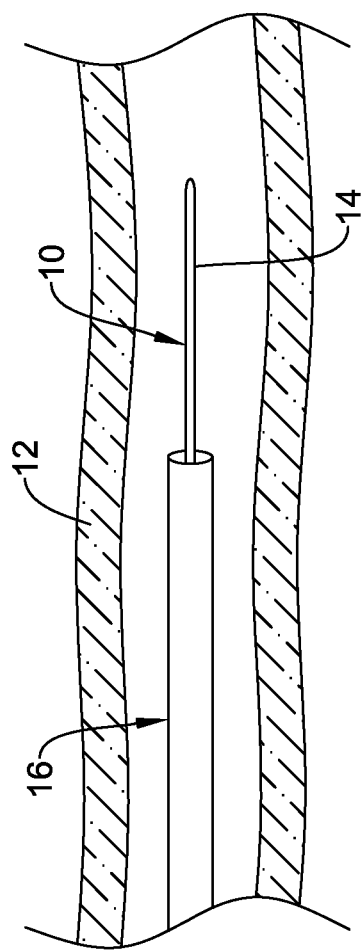
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Figure 2:
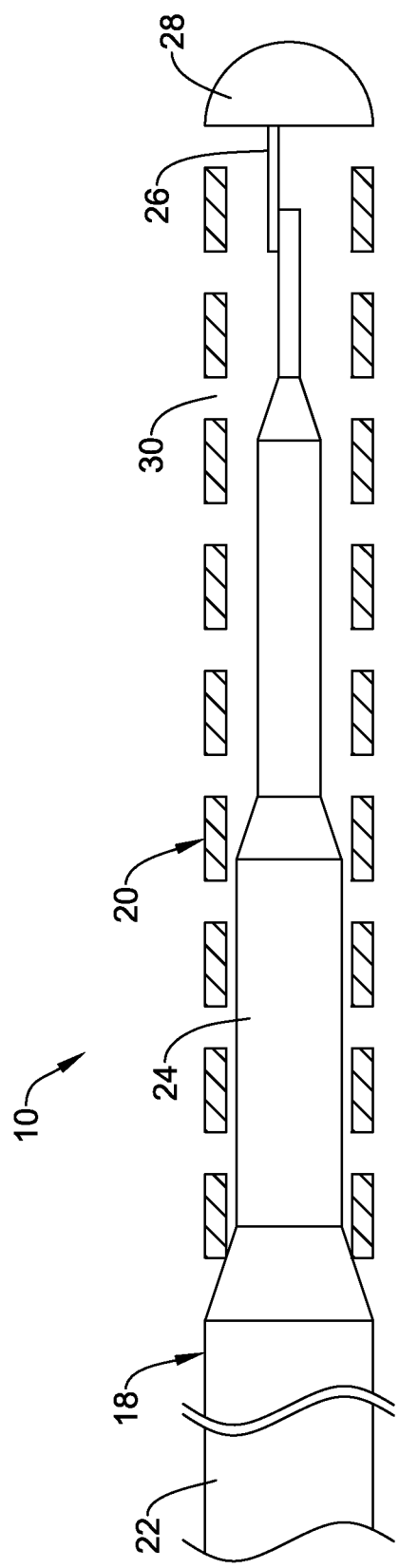
FIG. 2 is a partial cross-sectional side view of an example medical device.

FIG. 2 is a partial cross-sectional view of guidewire 10. Here it can be seen that guidewire 10 may include a core member or core wire 18 and a tubular member 20 disposed over at least a portion of core wire 18. Tubular member 20 may have a plurality of slots 30 formed therein. Core wire 18 may include a proximal section 22 and a distal section 24. A connector (not shown) may be disposed between and attach proximal section 22 to distal section 24. Alternatively, core wire 18 may be a unitary member without a connector. A shaping member 26 may be coupled to core wire 18 (for example distal section 24 of core wire 18), tubular member 20, or both. Shaping member 26 may be made from a relatively inelastic material so that a clinician can bend or shape the distal end of guidewire 10 into a shape that may facilitate navigation of guidewire 10 through the anatomy. Some examples of suitable materials for core wire 18, tubular member 20, shaping member 26, etc. can be found below. A tip member 28 may also be coupled to core wire 18, tubular member 20, or both that may define an atraumatic distal tip of guidewire 10. In general, tip member 28 may include solder. However, other versions of tip member 28 are contemplated including tip members 28 that comprise or form a polymeric tip.

Figure 3:
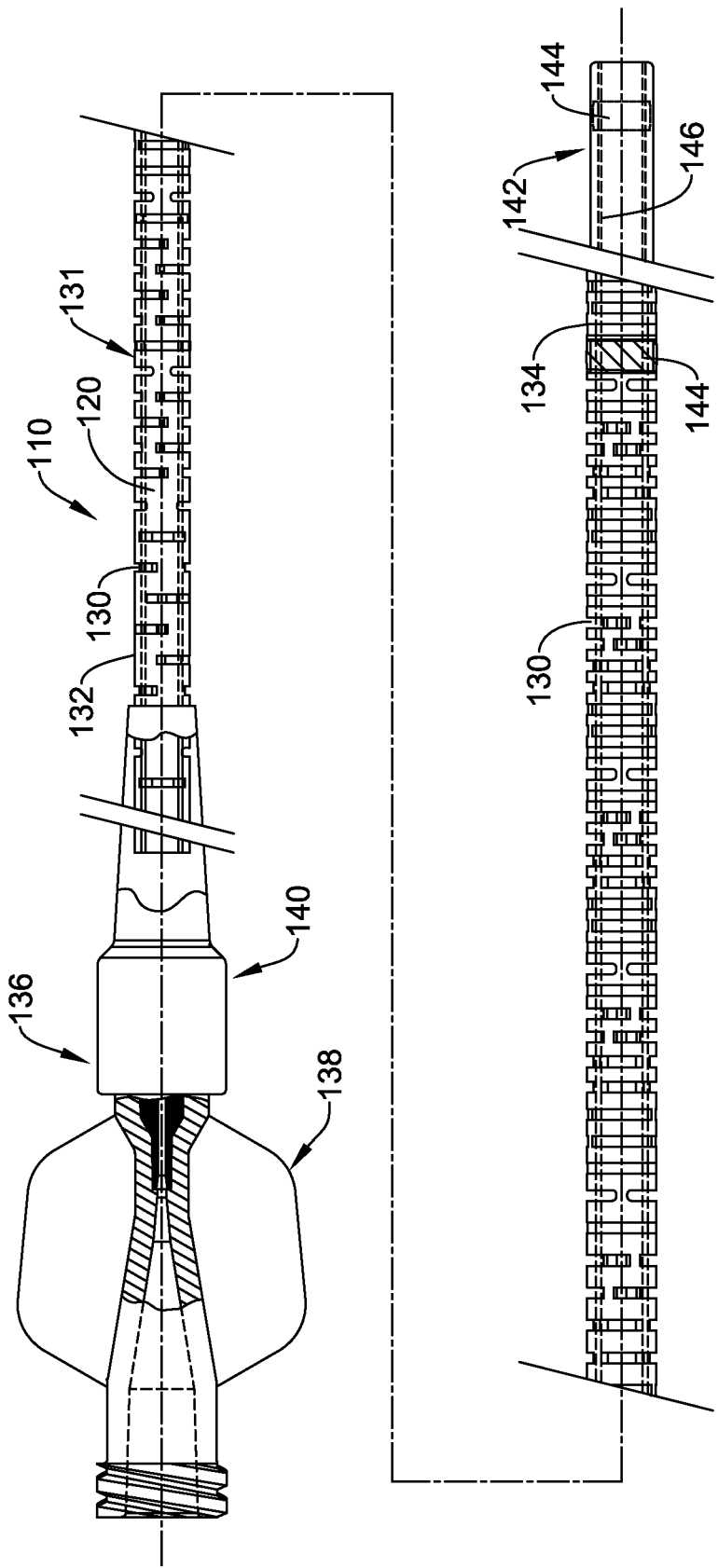
FIG. 3 is a partial cross-sectional side view of another example medical device.

Although medical device 10 is depicted in FIG. 1 as a guidewire, it is not intended to be limited to just being a guidewire. Indeed, medical device 10 may take the form of any suitable guiding, diagnosing, or treating device (including catheters, endoscopic instruments, laparoscopic instruments, etc., and the like) and it may be suitable for use at essentially any location and/or body lumen within a patient. For example, FIG. 3 illustrates another example device 110 in the form of a catheter. Catheter 110 may include a generally elongate shaft 131 having a proximal portion 132 and a distal portion 134. A proximal manifold 136 may be disposed at proximal portion 132. Manifold 136 may include a hub 138 and strain relief 140. A tip member 142 may be disposed at distal portion 134. Tip member 142 may include a radiopaque marker member 144. One or more additional marker members 144 may be disposed along other portions of catheter 110, for example along distal portion 134 of shaft 131. Shaft 131 may include a tubular member 120 that may be similar in form and function to other tubular members disclosed herein including tubular member 20. Tubular member 120 may have a plurality of slots 130 formed therein. A liner 146 may be disposed within tubular member 120. Liner 146 may be similar to the analogous structure disclosed in U.S. Pat. No. 7,001,369 and U.S. Patent Application Publication No. US 2006/0264904, the entire disclosures of which are herein incorporated by reference.

As indicated above, tubular member 20 (and/or other tubular members disclosed herein) may include a plurality of cuts, apertures, and/or slots 30 formed therein. Various embodiments of arrangements and configurations of slots 30 are contemplated. In some embodiments, at least some, if not all of slots 30 are disposed at the same or a similar angle with respect to the longitudinal axis of tubular member 20. As shown, slots 30 can be disposed at an angle that is perpendicular, or substantially perpendicular, and/or can be characterized as being disposed in a plane that is normal to the longitudinal axis of tubular member 20. However, in other embodiments, slots 30 can be disposed at an angle that is not perpendicular, and/or can be characterized as being disposed in a plane that is not normal to the longitudinal axis of tubular member 20. Additionally, a group of one or more slots 30 may be disposed at different angles relative to another group of one or more slots 30. The distribution and/or configuration of slots 30 can also include, to the extent applicable, any of those disclosed in U.S. Pat. Publication No. US 2004/0181174, the entire disclosure of which is herein incorporated by reference.

Slots 30 may be provided to enhance the flexibility of tubular member 20 while still allowing for suitable torque transmission characteristics. Slots 30 may be formed such that one or more rings and/or tube segments interconnected by one or more segments and/or beams that are formed in tubular member 20, and such tube segments and beams may include portions of tubular member 20 that remain after slots 30 are formed in the body of tubular member 20. Such an interconnected structure may act to maintain a relatively high degree of torsional stiffness, while maintaining a desired level of lateral flexibility. In some embodiments, some adjacent slots 30 can be formed such that they include portions that overlap with each other about the circumference of tubular member 20. In other embodiments, some adjacent slots 30 can be disposed such that they do not necessarily overlap with each other, but are disposed in a pattern that provides the desired degree of lateral flexibility.

Additionally, slots 30 can be arranged along the length of, or about the circumference of, tubular member 20 to achieve desired properties. For example, adjacent slots 30, or groups of slots 30, can be arranged in a symmetrical pattern, such as being disposed essentially equally on opposite sides about the circumference of tubular member 20, or can be rotated by an angle relative to each other about the axis of tubular member 20. Additionally, adjacent slots 30, or groups of slots 30, may be equally spaced along the length of tubular member 20, or can be arranged in an increasing or decreasing density pattern, or can be arranged in a non-symmetric or irregular pattern. Other characteristics, such as slot size, slot shape and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section 26, or a distal section 28, or the entire tubular member 20, may not include any such slots 30.

As suggested above, slots 30 may be formed in groups of two, three, four, five, or more slots 30, which may be located at substantially the same location along the axis of tubular member 20. Alternatively, a single slot 30 may be disposed at some or all of these locations. Within the groups of slots 30, there may be included slots 30 that are equal in size (i.e., span the same circumferential distance around tubular member 20). In some of these as well as other embodiments, at least some slots 30 in a group are unequal in size (i.e., span a different circumferential distance around tubular member 20). Longitudinally adjacent groups of slots 30 may have the same or different configurations. For example, some embodiments of tubular member 20 include slots 30 that are equal in size in a first group and then unequally sized in an adjacent group. It can be appreciated that in groups that have two slots 30 that are equal in size and are symmetrically disposed around the tube circumference, the centroid of the pair of beams (i.e., the portion of tubular member 20 remaining after slots 30 are formed therein) is coincident with the central axis of tubular member 20. Conversely, in groups that have two slots 30 that are unequal in size and whose centroids are directly opposed on the tube circumference, the centroid of the pair of beams is offset from the central axis of tubular member 20. Some embodiments of tubular member 20 include only slot groups with centroids that are coincident with the central axis of the tubular member 20, only slot groups with centroids that are offset from the central axis of tubular member 20, or slot groups with centroids that are coincident with the central axis of tubular member 20 in a first group and offset from the central axis of tubular member 20 in another group. The amount of offset may vary depending on the depth (or length) of slots 30 and can include essentially any suitable distance.

Slots 30 can be formed by methods such as micro-machining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 20 is formed by cutting and/or removing portions of the tube to form slots 30. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 30 in tubular member 20 using any of these or other manufacturing steps.

In at least some embodiments, slots 30 may be formed in tubular member using a laser cutting process. The laser cutting process may include essentially any suitable laser and/or laser cutting apparatus. For example, the laser cutting process may utilize a fiber laser. Utilizing processes like laser cutting may be desirable for a number of reasons. For example, laser cutting processes may allow tubular member 20 to be cut into a number of different cutting patterns in a precisely controlled manner. This may include variations in the slot width (which also may be termed "kerf"), ring width, beam height and/or width, etc. Furthermore, changes to the cutting pattern can be made without the need to replace the cutting instrument (e.g., a blade). This may also allow smaller tubes (e.g., having a smaller outer diameter) to be used to form tubular member 20 without being limited by a minimum cutting blade size. Consequently, tubular members 20 may be fabricated for use in neurological devices or other devices where a small size may be desired.

Figure 4:
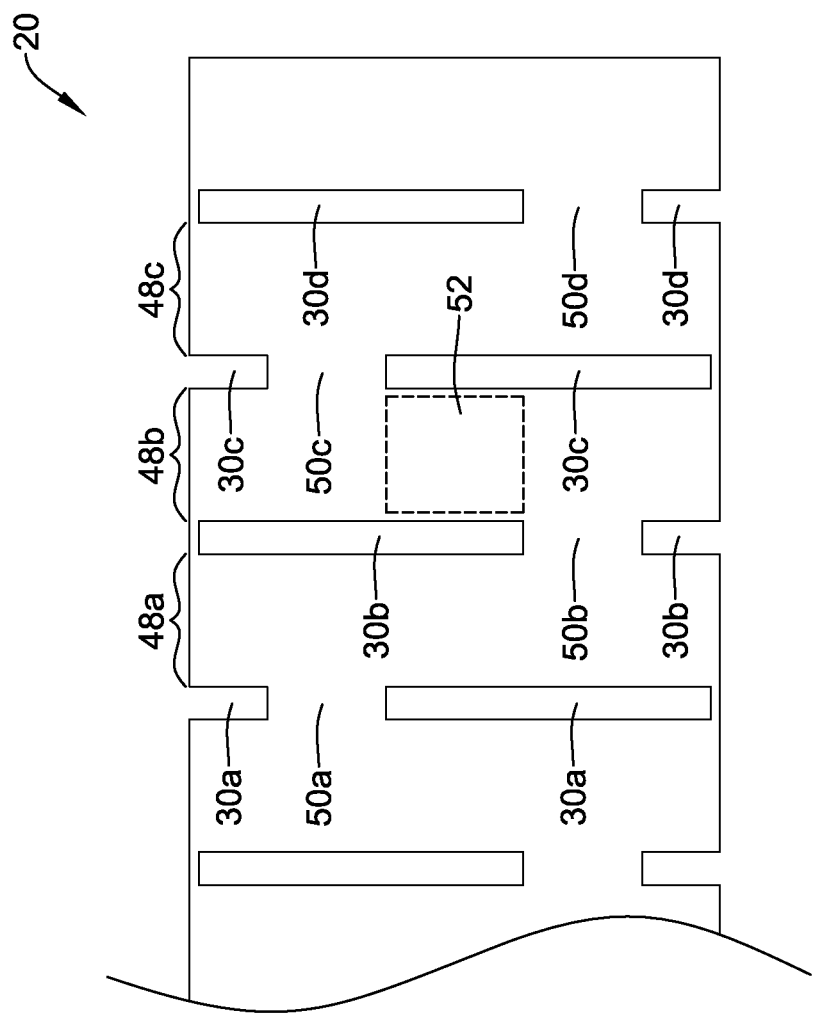
FIG. 4 is a side view of an example tubular member.

Because of the precision and control that may be achieved by cutting slots 30 with a laser, numerous additional variation can be achieved in slot 30 configurations, arrangements, etc. Turning now to FIG. 4, a side view of tubular member 20 is illustrated. In this figure and the accompanying description, some of the structural aspects of tubular member 20 are defined and described for the purposes of this disclosure. Here it can be seen that tubular member 20 may include a plurality of circumferential tube segments including tube segment 48a, tube segment 48b, and tube segment 48c. In this example, segment 48a is disposed longitudinally-adjacent (i.e., right next to) segment 48b and segment 48c is disposed longitudinally-adjacent segment 48b (oppositely segment 48a). The number of tube segments in a given tubular member 20 may vary depending on the structure of tubular member 20. For example, as the number of slots 30 increases, the number of tube segments may similarly increase. The invention is not intended to be limited to any particular number or arrangement of tube segments for any given tubular member 20 or device including a tubular member.

Segments 48a/48b/48c can be understood to be generally circumferential or "round" portions of tubular member 20 that are defined between groups or sets of slots 30. For example, segment 48a is defined between a first group of slots 30a and a second group of slots 30b. Likewise, segment 48b is defined between group 30b and a third group of slots 30c. Moreover, segment 48c is defined between group 30c and a fourth group of slots 30d. In this example, each group 30a/30b/30c/30d includes two slots. However, any suitable number of slots 30 may be utilized for any group 30a/30b/30c/30d. Just like the tube segments, the invention is not intended to be limited to any number of slots, groups of slots, or number of slots per group for any given tubular member 20 or device including a tubular member with slots.

When slots 30 are formed in tubular member, a portion of tubular member 20 remains at the longitudinal location where slots 30 are formed and extends between longitudinally-adjacent tube segments. This portion may be termed a "beam". Several beams are illustrated in FIG. 4 including beam 50a, beam 50b, beam 50c, and beam 50d. Beams 50a/50b/50c/50d can be understood to be a portion of tubular member 20 that connects or attaches longitudinally-adjacent tube segments. For example, segment 48b is attached to segment 48a by beam 50b. Similarly, segment 48b is attached to segment 48c by beam 50c. In this example, each group 30a/30b/30c/30d of slots defines or leaves behind two, corresponding beams at a given longitudinal location. In FIG. 4, which illustrates tubular member 20 from the side, often only one full beam can be seen. It can be appreciated that another beam may be defined in tubular member 20 on a portion of tubular member 20 that is not illustrated in FIG. 4 (e.g., the "back" or opposite side of tubular member 20). In addition, just like group 30a/30b/30c, the invention is not intended to be limited to any number of beams, groups of beams, or number of beams per group for any given tubular member 20 or device including a tubular member with beams.

Finally, along any given tube segment, one or more rings 52 may be defined. A ring 52 may be understood to be a portion of a tube segment that extends between two beams, for example a pair of beams on opposite sides of the tube segment. For example, a first or proximally-extending beam 50b and a second or distally-extending beam 50c may extend in opposite directions from tube segment 48b. Between beams 50b/50c, ring 52 may be defined. Using this same definition, several other "rings" may be seen and may be defined in tubular member 20.

In typical slotted tubular members, bending stresses that might be applied to the tube tend to be greater adjacent the beams. Similarly, torsional loading or stresses also tends to be greater adjacent the beams, although the tube segments and rings tend to have compressive and tensile loading along their centerline axes (e.g., radially aligned relative to the tube center). It may be desirable to change the stress distribution in a tubular member so that, for example, stresses are not localized to just one locale such as adjacent the beams. Accordingly, tubular member 20 may include one or more structural variations that may help to distribute stresses throughout tubular member 20. For example, tubular member 20 may include one or more structural variations that may help distribute stresses in a substantially uniform manner throughout tubular member 20.

Figure 5:
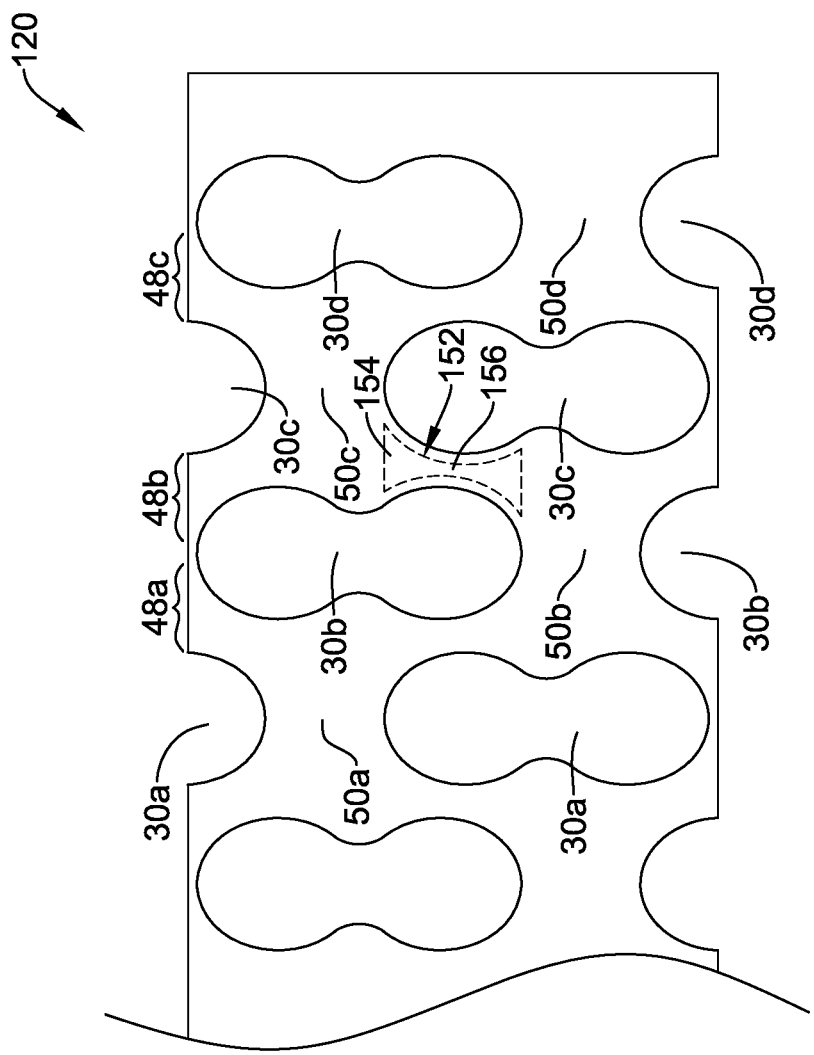
FIG. 5 is a side view of another example tubular member.

In some embodiments, the shape of the rings may be varied to help distribute stresses throughout the tubular member. For example, FIG. 5 illustrates tubular member 120, that may be similar in form and function to other tubular members disclosed herein, where at least one of the rings 152 has a first portion 154 having a first width and a second portion 156 having a second width different from the first width. In at least some embodiments, the first width 154 is larger (wider) than the second width 156, as illustrated. This may result in ring 152 having an hourglass shape or likeness. This may also be described as a varying or changing width for ring 152. Other arrangements, of course are contemplated including the reverse arrangement or other configurations. The changes in width may occur in any suitable manner including linearly, in a curved or curvilinear manner, in a parabolic manner, in a stepwise manner, combinations thereof, or the like.

By virtue of tubular member 120 having ring 152 with a varying width, stress in bending and/or torsional loading that might otherwise tend to be localized to positions adjacent beams 150 may be distributed more evenly throughout tubular member 120. In addition, such a configuration may have a minimal or relatively small impact on torsional stiffness because the rings and/or tube segments may be loaded substantially in compression/tension during torsional structural loading. Consequently, tubular member 120 may having an improved fatigue life, improved and/or increased strength, and/or other desirable properties.

Complex ring structures like ring 152 may be challenging, if not impossible to form using conventional saw-cutting or micromachining techniques. Consequently, forming ring 152 may include the use of a laser and/or laser cutting techniques, as suggested above. Such techniques may desirably allow for a plethora of differently shaped slot, beam, tube segment, and ring configurations. In addition, such laser cutting techniques may allow for additional changes to tubular members as will be elaborated on further below.

Figure 6:
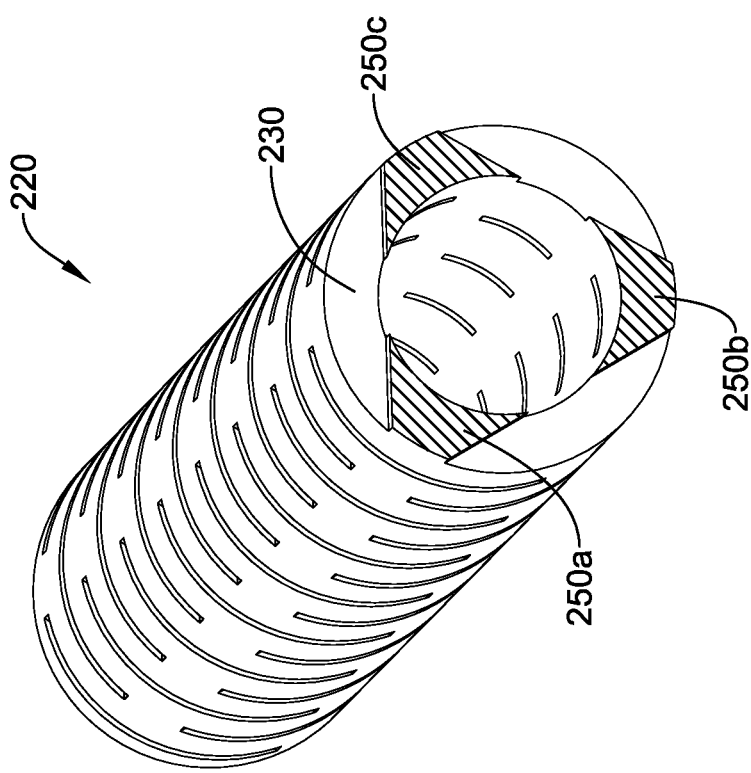
FIG. 6 is a partial cross-sectional view of another example tubular member.

FIG. 6 illustrates a tubular member 220 that includes slots 230 (arranged in groups of three slots 230 at each longitudinal location along tubular member 220) formed by saw cutting or micromachining Here it can be seen that the resultant beams 250a/250b/250c have a more irregular or triangular shape. The shape of beams 250a/250b/250c may result because of the nature of using a blade and/or the blade geometry and its approach tangent to the surface of tubular member 220. Because of the shape of beams 250a/250b/250c, stresses may not be evenly distributed across tubular member 220. Moreover, the blade geometry may limit the number of cuts and/or beams that can be formed at any given longitudinal position along tubular member 220. For example, it may be only possible to get three slots and/or beams at any given longitudinal location along tubular member 220 using saw cutting or micromachining.

Figure 7:
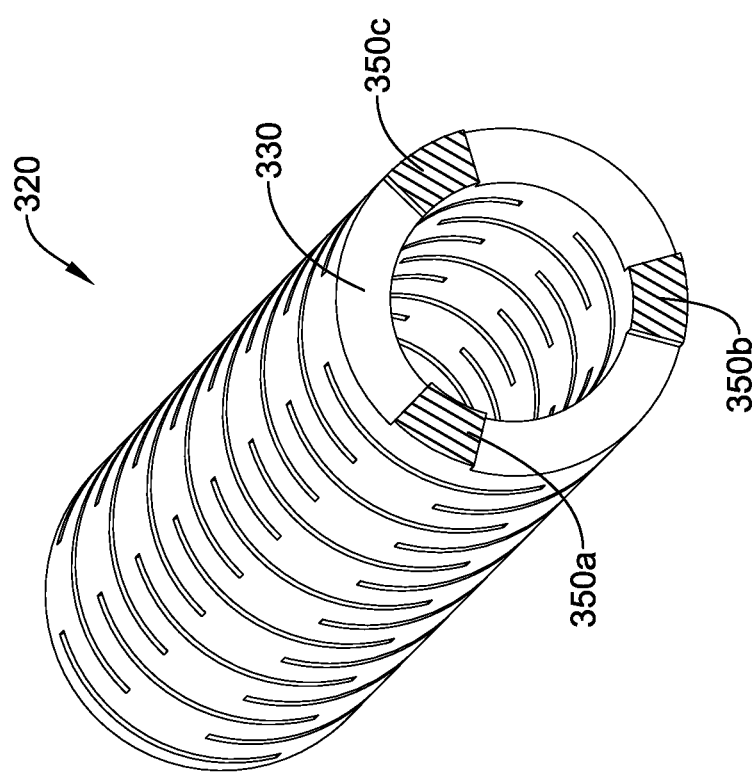
FIG. 7 is a partial cross-sectional view of another example tubular member.
Figure 8:
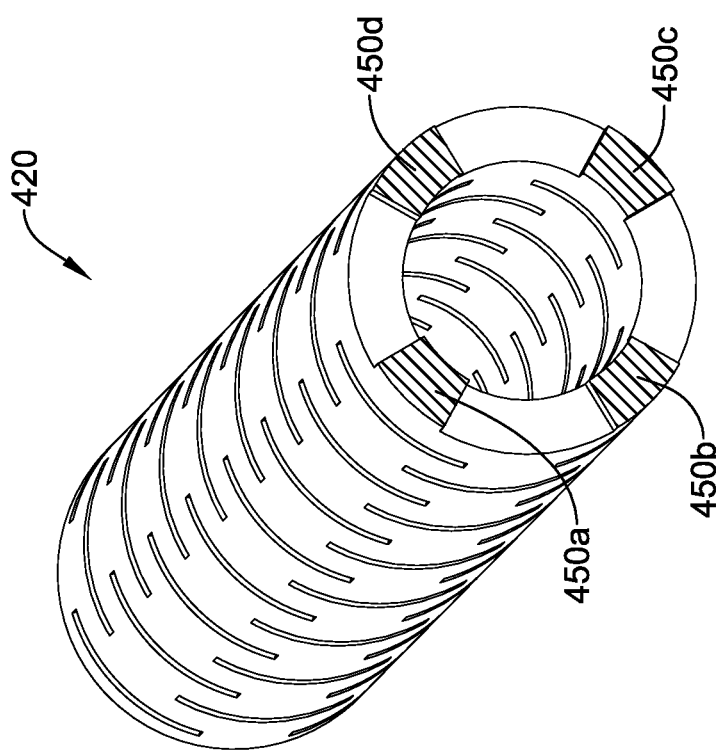
FIG. 8 is a partial cross-sectional view of another example tubular member.
Figure 9:
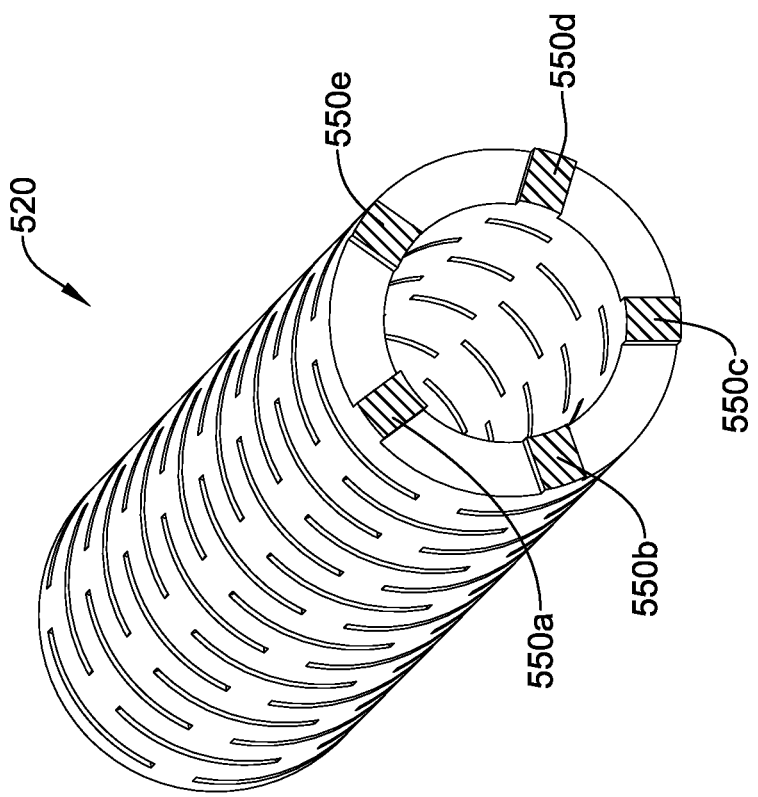
FIG. 9 is a partial cross-sectional view of another example tubular member.

FIG. 7 illustrates tubular member 320 that also includes slots 330 (arranged in groups of three slots 330 at each longitudinal location along tubular member 320) formed by laser cutting. Here it can be seen that the shape of the resultant beams 350a/350b 350c is more even or square-like in shape. This may result in improved stress distribution throughout tubular member 320. Furthermore, utilizing laser cutting techniques may allow for additional numbers of beams to formed in tubular members. For example, FIG. 8 illustrates tubular member 420 with a four beam 450a/450b/450c/450d structure and FIG. 9 illustrates tubular member 520 with a five beam 550a/550b/550c/550d/550e structure. Other tubular members are contemplated that include more beams and/or different arrangements or configurations of beams.

The materials that can be used for the various components of guidewire 10 (and/or other guidewires disclosed herein) and the various tubular members disclosed herein may include those commonly associated with medical devices. For simplicity purposes, the following discussion makes reference to tubular member 20 and other components of guidewire 10. However, this is not intended to limit the invention as the discussion may be applied to other similar tubular members and/or components of tubular members or devices disclosed herein.

Tubular member 20 and/or other components of guidewire 10 may be made from a metal, metal alloy, polymer (some examples of which are disclosed below), a metal-polymer composite, ceramics, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel.

One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 20 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of MRI compatibility is imparted into guidewire 10. For example, to enhance compatibility with Magnetic Resonance Imaging (MRI) machines, it may be desirable to make core wire 18 and/or tubular member 20, or other portions of the guidewire 10, in a manner that would impart a degree of MRI compatibility. For example, core wire 18 and/or tubular member 20, or portions thereof, may be made of a material that does not substantially distort the image and create substantial artifacts (artifacts are gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using any suitable connecting techniques and/or with a connector. For example, the different portions of core wire 18 can be connected using welding (including laser welding), soldering, brazing, adhesive, or the like, or combinations thereof. These techniques can be utilized regardless of whether or not a connector is utilized. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Essentially any suitable configuration and/or structure can be utilized for connector 26 including those connectors described in U.S. Pat. Nos. 6,918,882 and 7,071,197 and/or in U.S. Patent Pub. No. 2006-0122537, the entire disclosures of which are herein incorporated by reference.

A sheath or covering (not shown) may be disposed over portions or all of core wire 18 and/or tubular member 20 that may define a generally smooth outer surface for guidewire 10. In other embodiments, however, such a sheath or covering may be absent from a portion of all of guidewire 10, such that tubular member 20 and/or core wire 18 may form the outer surface. The sheath may be made from a polymer or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the guidewire 10 (including, for example, the exterior surface of core wire 18 and/or the exterior surface of tubular member 20) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of core wire 18 and/or tubular member, or other portions of device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The same may be true of tip member 28. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical device, comprising:
an elongate tubular member including a first circumferential tube segment, a second circumferential tube segment disposed next to the first circumferential tube segment, and a third circumferential tube segment disposed next to the second circumferential tube segment;
wherein the first tube segment and the second tube segment are separated by a first pair of opposed slots both formed in the tubular member at a first longitudinal position along the tubular member;
wherein the second tube segment and the third tube segment are separated by a second pair of opposed slots both formed in the tubular member at a second longitudinal position along the tubular member;
wherein each of the slots includes a first rounded region having a first width, a second rounded region having a second width the same as the first width, and a middle region between the first rounded region and the second rounded region having a third width smaller than the first width;
wherein the second tube segment is connected to the first tube segment with a proximally-extending beam having a first longitudinal axis and being formed in the tubular member;
wherein the second tube segment is also connected to the third tube segment with a distally-extending beam having a second longitudinal axis and being formed in the tubular member, wherein the first and second longitudinal axes are circumferentially offset from each other and wherein each of the first and second longitudinal axes intersects at least one beam and at least one slot;

wherein a ring is defined in the second tube segment between the proximally-extending beam and the distally-extending beam; and wherein the ring has a first portion with a first width, a second portion with a second width different from the first width, and a third portion with a third width that is the same as the first width.

2. The medical device of claim 1, wherein the medical device is a guidewire.

3. The medical device of claim 1, wherein the medical device is a catheter.

4. The medical device of claim 1, wherein the tubular member includes a nickel-titanium alloy.

5. The medical device of claim 1, wherein the first tube segment includes a second ring that has a varying width.

6. The medical device of claim 1, wherein the third tube segment includes a third ring that has a varying width.

7. The medical device of claim 1, wherein the second tube segment includes one or more additional rings with a varying width.

8. The medical device of claim 1, wherein the first width is greater than the second width.

9. The medical device of claim 8, wherein the first portion is disposed adjacent the proximally-extending beam.

10. The medical device of claim 8, wherein the first portion is disposed adjacent the distally-extending beam.

11. The medical device of claim 8, wherein the first width is the largest width of the ring.

12. The medical device of claim 8, wherein the second width is the smallest width of the ring.

13. The medical device of claim 8, wherein the second portion is disposed a distance away from both the proximally-extending beam and the distally-extending beam.

14. The medical device of claim 13, wherein the second portion is disposed midway between the proximally-extending beam and the distally-extending beam.

15. A medical device, comprising:
an elongate tubular member including a plurality of circumferential tube segments that are each defined between two longitudinally-adjacent sets of at least two slots each formed in the tubular member, the at least two slots of each set being disposed at a single longitudinal position along the tubular member;
wherein each slot includes a first rounded region having a first width, a second rounded region having a second width the same as the first width, and a middle region between the first rounded region and the second rounded region having a third width smaller than the first width;
wherein longitudinally-adjacent tube segments are connected together by flanking sets of beams that are disposed on opposite sides of each tube segment and that are circumferentially offset from one another;
wherein each tube segment includes one or more rings that are defined between a pair of beams on opposing sides of the tube segment; and
wherein at least one of the one or more rings has a varying width and has an hourglass shape, wherein each beam has a longitudinal axis extending parallel to a longitudinal axis of the elongate tubular member, each beam axis extending through at least one slot, and wherein each beam has a varying height along its longitudinal axis from a first end to a second of the beam.

16. The medical device of claim 15, wherein the ring having the varying width includes a first width and a second width, wherein the first width is greater than the second width.

17. The medical device of claim 16, wherein the first width is the maximum width of the ring and the second width is the minimum width of the ring.

18. The medical device of claim 17, wherein the first width is disposed adjacent one of the beams.

19. The medical device of claim 18, wherein the second width is disposed midway between a proximally-extending beam and a distally-extending beam.

20. A slotted tubular member for use in a medical device, comprising:
a tubular member including a first circumferential tube segment, a second circumferential tube segment disposed next to the first circumferential tube segment, and a third circumferential tube segment disposed next to the second circumferential tube segment;
a first set of at least two slots defined in the tubular member and positioned between the first tube segment and the second tube segment at a first longitudinal position along the tubular member, each of the first set of at least two slots having a first rounded upper portion having a first width, a first rounded lower portion having the first width, and a first narrow portion between the first upper portion and the first lower portion having a second width smaller than the first width;
a second set of at least two slots defined in the tubular member and positioned between the second tube segment and the third tube segment at a first longitudinal position along the tubular member, each of the second set of at least two slots having a second rounded upper portion having the first width, a second rounded lower portion having the first width, and a second narrow portion between the second upper portion and the second lower portion having a second width smaller than the first width;
wherein a first beam is formed in the tubular member and extends between the first tube segment and the second tube segment;
wherein a second beam is formed in the tubular member and extends between the second tube segment and the third tube segment, wherein the second beam is circumferentially offset from the first beam;
wherein each of the first beam and the second beam has a longitudinal axis extending parallel to a longitudinal axis of the elongate tubular member, each beam axis extending through at least one slot, and wherein each beam has a varying height along its longitudinal axis from a first end to a second of the beam;
wherein a ring is defined in the second tube segment between the first beam and the second beam;
wherein the ring is disposed between the first upper portion of one of the first set of at least two slots and the second lower portion of one of the second set of at least two slots;
wherein the ring has a varying width and has an hourglass shape.

* * * * *

UNITED STATES PATENT AND TRADEMARK OFFICE
CERTIFICATE OF CORRECTION

PATENT NO. : 8,795,254 B2  
APPLICATION NO. : 12/635577  
DATED : August 5, 2014  
INVENTOR(S) : Layman et al.

Page 1 of 1

It is certified that error appears in the above-identified patent and that said Letters Patent is hereby corrected as shown below:

In the Specification

Column 9  
Line 49: after "of about -60°C", delete "."  
Line 49: after "to about 120°C", delete "."

Signed and Sealed this  
Twenty-first Day of October, 2014

Michelle K. Lee  
*Deputy Director of the United States Patent and Trademark Office*